United States Patent [19]

Rattie et al.

[11] 4,255,413

[45] Mar. 10, 1981

[54] GELATIN CAPSULE DOSAGE UNIT CONTAINING TRIAMTERENE

[75] Inventors: Elisabeth S. Rattie, Abington; Louis J. Ravin, Plymouth Meeting, both of Pa.

[73] Assignee: SmithKline Corporation, Philadelphia, Pa.

[21] Appl. No.: 80,592

[22] Filed: Oct. 1, 1979

[51] Int. Cl.³ .................... A61K 9/48; A61K 31/505; A61K 31/54
[52] U.S. Cl. ..................................... 424/37; 424/156; 424/246; 424/251; 424/329
[58] Field of Search ................. 424/37, 156, 246, 251, 424/329

[56] References Cited

U.S. PATENT DOCUMENTS 3,081,230   3/1963   Weinstock ........................... 424/251

OTHER PUBLICATIONS

Ravin et al., J. of Pharm. Sci., vol. 58, 1969, pp. 1242–1245.
Stewart et al., J. Pharm. Pharmacol. vol. 31, 1979 pp. 1–6.
Newton et al., J. Pharm. Pharmacol,. vol. 26(s) pp. 30P–36P.

*Primary Examiner*—Anna P. Fagelson
*Attorney, Agent, or Firm*—Joseph A. Marlino; Richard D. Foggio; Alan D. Lourie

[57] ABSTRACT

A gelatin capsule unit dosage form containing triamterene, 2,4,7-triamino-6-phenylpteridine, which results in rapid dissolution of the active ingredient. The dosage form comprises the addition of a combination of a surfactant and a carbonate or bicarbonate salt as diluents.

7 Claims, No Drawings

GELATIN CAPSULE DOSAGE UNIT CONTAINING TRIAMTERENE

This invention relates to gelatin capsule dosage forms which contain triamterene as the active ingredient. Triamterene is a nonmercurial, orally effective diuretic which does not enhance the excretion of potassium. Further, triamterene potentiates the action of other diuretics and the combinations also restrict the loss of potassium due to their action. A still further utility for triamterene is the lowering of blood pressure, i.e., an antihypertensive agent.

The formulation of a poorly soluble-low dose medicament such as triamterene in a gelatin capsule presents several problems. Due to the dose of the medicament, it is necessary to add diluents in order to get the bulk required to fill the capsule. A disadvantage of this is that many diluents interfere with the release of the medicament.

A further disadvantage in the release of a poorly soluble medicament such as triamterene from gelatin capsules is that during the hydration, the gelatin forms a viscous barrier. This results in the formation of a plug or coagulation of the capsule ingredients which in turn results in poor dispersion and dissolution of the active ingredient. Instead of obtaining a maximum surface area for the drug, which is one of the prerequisites for increased solubility, a minimum surface area is obtained. A very erratic dissolution rate of the medicament results.

It is therefore the object of this invention to provide a gelatin capsule dosage form of triamterene which provides a significantly better dispersion and faster dissolution of the medicament resulting in better absorption and bioavailability.

It has been unexpectedly discovered that the combination of a surfactant and carbonate or bicarbonate salt as diluents in a triamterene gelatin capsule dosage form overcomes the above stated problems. Instead of a plug of the ingredients forming upon hydration of the gelatin, rapid dispersion of the ingredients takes place. A maximum surface area of triamterene is provided which results in a dramatic increase in dissolution.

The compositions of this invention as described above are advantageously carried out in conjunction with another non-pteridine diuretic, particularly with a thiazide diuretic. Exemplary of such thiazide derivatives are chlorothiazide, hydrochlorothiazide, flumethiazide, hydroflumethiazide, benzylhydroflumethiazide, trichloromethiazide or benzthiazide.

Advantageously the triamterene will be present in the capsule in an amount of from about 10 mg. to about 100 mg. and the thiazide compound of from about 2 mg. to about 250 mg.

Following are in vitro test results comparing the dissolution rate of capsule dosage forms containing triamterene with a variety of diluents.

TABLE I

| Ingredients (mg./capsule) | I | II | III | IV | V | VI | VII |
| --- | --- | --- | --- | --- | --- | --- | --- |
| Triamterene | 50 | 50 | 50 | 50 | 50 | 50 | 50 |
| Hydrochlorothiazide | 25 | — | 25 | — | 25 | 25 | 25 |
| Lactose | 91.8 | 101 | 44 | — | — | — | — |
| Magnesium Stearate | 3.2 | 1.5 | 1.6 | 1.6 | 1.6 | 1.6 | 1.6 |
| Calcium Carbonate | — | — | 44 | 44.2 | 44.2 | — | 44.2 |
| Sodium Carboxymethyl starch | — | — | — | 69.2 | 47.6 | 88 | 44.2 |
| Cetyldimethylpyridinium Chloride | — | — | 3.4 | 3.4 | — | 3.4 | 3.4 |

All formulas were tested in a #4 hard gelatin capsule.

TABLE II

| Formula | Percent Triamterene Dissolved | | | |
| --- | --- | --- | --- | --- |
| | 5 minutes | 10 minutes | 20 minutes | 30 minutes |
| I | 0 | 0 | 5 | 8 |
| II | 0 | 0 | 2 | 4 |
| III | 15 | 70 | 93 | 97 |
| IV | 53 | 89 | 97 | 99 |
| V | 6 | 37 | 54 | 67 |
| VI | 45 | 65 | 74 | 85 |
| VII | 55 | 82 | 97 | 98 |

The above dissolution rate studies were performed by the USP Paddle Method in 900 ml. of artificial gastric fluid without enzyme at 37° C. and 50 RPM. This test is detailed under Dissolution, Method II of the 4th Supplement, United States Pharmacopeia XIX, National Formulary XIV, page 194, released Jan. 31, 1978.

Referring specifically to the above Table I, it can be seen that Formulas I and II contain triamterene with hydrochlorothiazide and triamterene alone respectively. Both of these formulas have conventional capsule diluents present, i.e., lactose and magnesium stearate. It will be noted from Table II that only 8% and 4% of triamterene dissolves over a 30 minute period.

When calcium carbonate is present without the surfactant, Formula V, 67% of the triamterene dissolves in 30 minutes. When the surfactant is present without the carbonate, Formula VI, 85% dissolves in 30 minutes.

However, when calcium carbonate and a surfactant such as cetyldimethylpyridinium chloride are added to the formulas (III and IV), the dissolution rate of triamterene is increased to 99%.

The results of these tests clearly demonstrate that when both the carbonate and surfactant are added in combination to the gelatin dosage unit, a very dramatic increase in dissolution of the triamterene results, i.e., from 4% to 99% in 30 minutes.

In addition to calcium carbonate, it will be evident to one skilled in the pharmaceutical art that any nontoxic ammonium or alkali metal carbonate or bicarbonate salt may also be employed in this invention. Exemplary of such carbonates or bicarbonates are magnesium carbonate, sodium carbonate, potassium carbonate, or sodium bicarbonate. The salts will be present from about 6% to about 52% of the capsule formulation. Preferably the salts will be present from 12% to about 35%.

Exemplary of surfactants other than cetyldimethylpyridinium chloride which may be employed in this invention are Polysorbate derivatives such as Polysorbate 80, sodium lauryl sulfate and dioctyl sodium sulfosuccinate. The surfactant may be present in an amount of from about 0.15% to about 3.0% of the composition. Preferably the surfactant will be present from about 0.5 to 3.0%.

If desired, disintegrants such as starch or Veegum which are standard pharmaceutical excipients commonly used in capsule manufacturing may also be employed. Since these ingredients are not an essential aspect of this invention, the amount can be varied.

Advantageously the ingredients present in the Formulas of I through VII of Table I are mixed together and filled into a #4 hard gelatin capsule. If desired, these ingredients may also be encapsulated as granules. The granules may be produced by wetting the triamterene with a suitable granulating agent such as, for example, solutions of gelatin or polyvinylpyrrolidone. The wetted powder is passed through a #6 screen and dried overnight. The dried granules are then passed through a #14 standard screen, mixed with the diluents and filled into a #4 hard gelatin capsule.

What is claimed is:

1. A gelatin capsule dosage unit comprising triamterene, and a rapid dissolution and dispersing amount of a combination of a surfactant and a calcium, ammonium, or alkali metal nontoxic carbonate or bicarbonate salt.

2. The gelatin capsule of claim 1 in which the surfactant is cetyldimethylpyridinium chloride.

3. The gelatin capsule of claim 2 in which the carbonate salt is calcium carbonate.

4. The gelatin capsule of claim 1 in which triamterene is present in an amount of from 10 mg. to 100 mg., the surfactant is present in an amount of from 0.5% to about 3.0%, and the salt is present from about 12% to about 35%.

5. A gelatin capsule dosage unit comprising triamterene, hydrochlorothiazide, and a rapid dissolution and dispersing amount of a combination of a surfactant, and a calcium, ammonium, or alkali metal nontoxic carbonate or bicarbonate salt.

6. The gelatin capsule of claim 5 in which the surfactant is cetyldimethylpyridinium chloride and the carbonate salt is calcium carbonate.

7. The gelatin capsule of claim 6 in which the triamterene is present in an amount of from 10 mg. to 100 mg. and the hydrochlorothiazide is present in an amount of from 2 mg. to 250 mg.

* * * * *